United States Patent
Tirtowidjojo et al.

(10) Patent No.: US 9,512,053 B2
(45) Date of Patent: Dec. 6, 2016

(54) PROCESS FOR THE PRODUCTION OF CHLORINATED PROPENES

(71) Applicant: Blue Cube IP LLC, Midland, MI (US)

(72) Inventors: Max M. Tirtowidjojo, Lake Jackson, TX (US); David S. Laitar, Midland, MI (US); Barry B. Fish, Lake Jackson, TX (US); Matthew L. Grandbois, Midland, MI (US)

(73) Assignee: BLUE CUBE IP LLC, Midland, MI (US)

( * ) Notice: Subject to any disclaimer, the term of this patent is extended or adjusted under 35 U.S.C. 154(b) by 0 days.

(21) Appl. No.: 14/653,503

(22) PCT Filed: Dec. 18, 2013

(86) PCT No.: PCT/US2013/075909
§ 371 (c)(1),
(2) Date: Jun. 18, 2015

(87) PCT Pub. No.: WO2014/100066
PCT Pub. Date: Jun. 26, 2014

(65) Prior Publication Data
US 2015/0344386 A1    Dec. 3, 2015

Related U.S. Application Data

(60) Provisional application No. 61/738,787, filed on Dec. 18, 2012.

(51) Int. Cl.
| C07C 17/013 | (2006.01) |
| C07C 17/21 | (2006.01) |
| C07C 17/06 | (2006.01) |
| C07C 17/04 | (2006.01) |
| C07C 17/10 | (2006.01) |
| C07C 17/25 | (2006.01) |

(52) U.S. Cl.
CPC ............. *C07C 17/013* (2013.01); *C07C 17/04* (2013.01); *C07C 17/06* (2013.01); *C07C 17/10* (2013.01); *C07C 17/21* (2013.01); *C07C 17/25* (2013.01)

(58) Field of Classification Search
CPC ..... C07C 17/013; C07C 17/21; C07C 17/25; C07C 17/04; C07C 17/10
See application file for complete search history.

(56) References Cited

U.S. PATENT DOCUMENTS

| 2,119,484 A | 5/1938 | Levine et al. |
| 2,179,378 A | 11/1939 | Metzger |
| 2,207,193 A | 7/1940 | Groll |
| 2,299,441 A | 10/1942 | Vaughan et al. |
| 2,302,228 A | 11/1942 | Kharasch et al. |
| 2,370,342 A | 2/1945 | Zellner |
| 2,378,859 A | 6/1945 | Martin |
| 2,435,983 A | 2/1948 | Schmerling |
| 2,449,286 A | 9/1948 | Fairbairn |
| 2,588,867 A | 3/1952 | Morris |
| 2,630,461 A | 3/1953 | Sachsse et al. |
| 2,688,592 A | 9/1954 | Skeeters |
| 2,762,611 A | 9/1956 | Monroe |
| 2,765,359 A | 10/1956 | Pichler et al. |
| 2,964,579 A | 12/1960 | Weller et al. |
| 2,973,393 A | 2/1961 | Monroe |
| 3,000,980 A | 9/1961 | Asadorian |
| 3,094,567 A | 6/1963 | Eaker |
| 3,112,988 A | 12/1963 | Coldren et al. |
| 3,444,263 A | 5/1969 | Fernald |
| 3,446,859 A | 5/1969 | Weil |
| 3,502,734 A | 3/1970 | Baird |
| 3,525,595 A | 8/1970 | Zirngibl et al. |
| 3,551,512 A | 12/1970 | Loeffler |
| 3,558,438 A | 1/1971 | Schoenbeck |
| 3,651,019 A | 3/1972 | Asscher |
| 3,676,508 A | 7/1972 | Krekeler |
| 3,819,731 A | 6/1974 | Pitt |
| 3,823,195 A | 7/1974 | Smith |
| 3,872,664 A | 3/1975 | Lohmann |
| 3,914,167 A | 10/1975 | Ivy |
| 3,920,757 A | 11/1975 | Watson |
| 3,926,758 A | 12/1975 | Smith |
| 3,948,858 A | 4/1976 | Weirsum |

(Continued)

FOREIGN PATENT DOCUMENTS

| CH | 609022 | 6/1974 |
| CN | 101215220 | 7/2008 |

(Continued)

OTHER PUBLICATIONS

Michigan Technological Univ., "Free-Radical Chlorination with Sulfuryl Chloride", Nov. 15, 2001, 1-7.
Bai, et al., "Isomerization of Tetrachloropropene to Promote Utilization Ratio of Triallate Raw Materials", Petrochemical Technology & Application, 2007, 25(1).
Chai, et al., "Study of Preparation of 1,1,1,3-tetrachloropropane", Zhejiang Chemical Industry, 2010, pp. 1-3, 41(5).

(Continued)

*Primary Examiner* — Shailendra Kumar
(74) *Attorney, Agent, or Firm* — Polsinelli PC

(57) ABSTRACT

Processes for the production of chlorinated propenes are provided. The processes make use of 1,2-dichloropropane as a starting material and subject a feedstream comprising the same to an ionic chlorination process. At least a portion of any tri- and tetrachlorinated propanes not amenable to ionic chlorination conditions are removed from the ionic chlorination product stream, or, are subjected to chemical base dehydrochlorination step. In this way, recycle of intermediates not amenable to ionic chlorination reactions is reduced or avoided, as is the buildup of these intermediates within the process. Selectivity and, in some embodiments, yield of the process is thus enhanced.

17 Claims, 3 Drawing Sheets

(56) References Cited

U.S. PATENT DOCUMENTS

| | | |
|---|---|---|
| 3,954,410 A | 5/1976 | Pohl et al. |
| 4,038,372 A | 7/1977 | Colli |
| 4,046,656 A | 9/1977 | Davis et al. |
| 4,051,182 A | 9/1977 | Pitt |
| 4,319,062 A | 3/1982 | Boozalis et al. |
| 4,513,154 A | 4/1985 | Kurtz |
| 4,535,194 A | 8/1985 | Woodard |
| 4,614,572 A | 9/1986 | Holbrook |
| 4,644,907 A | 2/1987 | Hunter |
| 4,650,914 A | 3/1987 | Woodard |
| 4,661,648 A | 4/1987 | Franklin |
| 4,702,809 A | 10/1987 | Mueller |
| 4,714,792 A | 12/1987 | Muller et al. |
| 4,716,255 A | 12/1987 | Muller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Muller |
| 4,999,102 A | 3/1991 | Cox |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter et al. |
| 5,246,903 A | 9/1993 | Harley |
| 5,254,771 A | 10/1993 | Cremer |
| 5,254,772 A | 10/1993 | Dukat |
| 5,254,788 A | 10/1993 | Gartside |
| 5,262,575 A | 11/1993 | Dianis |
| 5,315,044 A | 5/1994 | Furutaka |
| 5,367,105 A | 11/1994 | Miyazaki et al. |
| 5,414,166 A | 5/1995 | Kim |
| 5,504,266 A | 4/1996 | Tirtowidjojo et al. |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,235,951 B1 | 5/2001 | Sakyu et al. |
| 6,472,573 B1 | 10/2002 | Yamamoto |
| 6,518,467 B2 | 2/2003 | Tung et al. |
| 6,538,167 B1 | 3/2003 | Brown |
| 6,545,176 B1 | 4/2003 | Tsay |
| 6,551,469 B1 | 4/2003 | Nair |
| 6,610,177 B2 | 8/2003 | Tsay |
| 6,613,127 B1 | 9/2003 | Galloway |
| 6,683,216 B1 | 1/2004 | Zoeller |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada |
| 7,345,209 B2 | 3/2008 | Mukhopadhyay |
| 7,371,904 B2 | 5/2008 | Ma et al. |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,836,941 B2 | 11/2010 | Song |
| 7,880,040 B2 | 2/2011 | Mukhopadhyay |
| 7,951,982 B2 | 5/2011 | Mukhopadhyay |
| 8,058,486 B2 | 11/2011 | Merkel et al. |
| 8,058,490 B2 | 11/2011 | Strebelle |
| 8,071,825 B2 | 12/2011 | Johnson et al. |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Tirtowidjojo |
| 8,258,355 B2 | 9/2012 | Merkel |
| 8,357,828 B2 | 1/2013 | Okamoto et al. |
| 8,367,867 B2 | 2/2013 | Zardi et al. |
| 8,383,867 B2 | 2/2013 | Mukhopadhyay |
| 8,395,000 B2 | 3/2013 | Mukhopadhyay |
| 8,398,882 B2 | 3/2013 | Rao |
| 8,487,146 B2 | 7/2013 | Wilson |
| 8,558,041 B2 | 10/2013 | Tirtowidjojo et al. |
| 8,581,011 B2 | 11/2013 | Tirtowidjojo et al. |
| 8,581,012 B2 | 11/2013 | Tirtowidjojo et al. |
| 8,614,361 B2 | 12/2013 | Suzuki |
| 8,614,363 B2 | 12/2013 | Wilson et al. |
| 8,907,148 B2 | 12/2014 | Tirtowidjojo et al. |
| 8,926,918 B2 | 1/2015 | Tirtowidjojo et al. |
| 8,933,280 B2 | 1/2015 | Tirtowidjojo et al. |
| 8,957,258 B2 | 2/2015 | Okamoto et al. |
| 9,056,808 B2 | 6/2015 | Tirtowidjojo et al. |
| 9,067,855 B2 | 6/2015 | Grandbois et al. |
| 2001/0018962 A1 | 9/2001 | Joshi et al. |
| 2002/0087039 A1 | 7/2002 | Tung et al. |
| 2002/0110711 A1 | 8/2002 | Boneberg et al. |
| 2005/0245774 A1 | 11/2005 | Mukhopadhyay et al. |
| 2006/0150445 A1 | 7/2006 | Redding |
| 2006/0292046 A1 | 12/2006 | Fruchey |
| 2007/0197841 A1 | 8/2007 | Mukhopadhyay |
| 2007/0197842 A1 | 8/2007 | Tung |
| 2007/0265368 A1 | 11/2007 | Rao et al. |
| 2008/0021229 A1 | 1/2008 | Maughon |
| 2008/0073063 A1 | 3/2008 | Clavenna et al. |
| 2008/0118018 A1 | 5/2008 | Schrauwen |
| 2008/0207962 A1 | 8/2008 | Rao |
| 2009/0018377 A1 | 1/2009 | Boyce |
| 2009/0030249 A1 | 1/2009 | Merkel et al. |
| 2009/0088547 A1 | 4/2009 | Schamschurin et al. |
| 2009/0099396 A1 | 4/2009 | Mukhopadhyay |
| 2009/0117014 A1 | 5/2009 | Carpenter |
| 2009/0203945 A1 | 8/2009 | Mukhopadhyay |
| 2009/0253946 A1 | 10/2009 | Van Der Puy |
| 2009/0270568 A1 | 10/2009 | Strebelle et al. |
| 2010/0041864 A1 | 2/2010 | Kadowaki et al. |
| 2010/0185029 A1 | 7/2010 | Elsheikh |
| 2010/0263278 A1 | 10/2010 | Kowoll et al. |
| 2011/0087056 A1 | 4/2011 | Tirtowidjojo et al. |
| 2011/0155942 A1 | 6/2011 | Pigamo et al. |
| 2011/0172472 A1 | 7/2011 | Sakyu |
| 2011/0218369 A1 | 9/2011 | Elsheikh et al. |
| 2011/0251425 A1 | 10/2011 | Penzel |
| 2012/0065434 A1 | 3/2012 | Nose |
| 2014/0081055 A1 | 3/2014 | Tirtowidjojo |
| 2014/0100394 A1* | 4/2014 | Tirtowidjojo ............ C07C 17/10 570/156 |
| 2014/0163266 A1 | 6/2014 | Tirtowidjojo et al. |
| 2014/0179962 A1 | 6/2014 | Tirtowidjojo et al. |
| 2014/0323775 A1 | 10/2014 | Grandbois et al. |
| 2014/0323776 A1 | 10/2014 | Grandbois et al. |
| 2014/0336425 A1 | 11/2014 | Tirtowdjojo et al. |
| 2014/0336431 A1 | 11/2014 | Tirtowidjojo et al. |
| 2014/0371494 A1 | 12/2014 | Tirtowidjojo et al. |
| 2015/0045592 A1 | 2/2015 | Grandbois et al. |
| 2015/0057471 A1 | 2/2015 | Tirtowidjojo et al. |
| 2015/0217256 A1 | 8/2015 | Tirtowidjojo et al. |

FOREIGN PATENT DOCUMENTS

| | | |
|---|---|---|
| CN | 101492341 | 7/2009 |
| CN | 101544535 | 9/2009 |
| CN | 101597209 | 12/2009 |
| CN | 101754941 | 6/2010 |

(56) References Cited

FOREIGN PATENT DOCUMENTS

| | | |
|---|---|---|
| CN | 101913979 | 12/2010 |
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |
| CN | 102351637 | 2/2012 |
| CN | 1035621264 A | 2/2014 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0131560 | 1/1985 |
| EP | 0164798 | 12/1985 |
| EP | 0453818 | 10/1991 |
| EP | 1018366 | 12/2000 |
| EP | 1097984 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| GB | 1548277 | 7/1979 |
| JP | 54079207 | 6/1979 |
| JP | S54-135712 | 10/1979 |
| JP | 08-119885 | 5/1996 |
| JP | 2001213820 | 8/2001 |
| JP | 2006272267 | 10/2006 |
| JP | 2007021396 | 2/2007 |
| JP | 2007-535561 | 12/2007 |
| JP | 2008063314 | 3/2008 |
| JP | 2009000592 | 1/2009 |
| JP | 2009046653 | 3/2009 |
| JP | 2001151708 | 6/2011 |
| JP | 2011144148 | 7/2011 |
| LU | 52247 | 12/1966 |
| SU | 899523 | 1/1982 |
| WO | 0138271 | 5/2001 |
| WO | 0138275 | 5/2001 |
| WO | 2005016509 | 2/2005 |
| WO | 2007079431 | 7/2007 |
| WO | 2007079435 | 7/2007 |
| WO | 2007096383 | 8/2007 |
| WO | 2008054781 | 5/2008 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 12/2012 |
| WO | 2012166393 | 12/2012 |
| WO | 2012166394 A1 | 12/2012 |
| WO | 2013082410 | 6/2013 |
| WO | 2014046970 | 3/2014 |
| WO | 2014046977 | 3/2014 |
| WO | 2014066083 | 5/2014 |
| WO | 2014100039 | 6/2014 |
| WO | 2014100066 | 6/2014 |
| WO | 2014134233 | 9/2014 |
| WO | 2014134377 | 9/2014 |
| WO | 2014164368 | 10/2014 |

OTHER PUBLICATIONS

Cristiano, et al., "Tetraalkylphosphonium Trihalides. Room Temperature Ionic Liquids As Halogenation Reagents", J. Org. Chem., 2009, pp. 9027-9033, 74.

Evstigneev, et al., "Initiated Chlorination of Tetrachloropropane", Khim. Prom., 1984, pp. 393-394, 16(7).

Fields, et al., "Thermal Isomerization of 1,1-dichlorocyclopropanes", Chemical Communications, Jan. 1, 1967, p. 1081, 21.

Galitzenstein, et al., "The Dehydrochlorination of Propylene Dichloride", Journal of the Society of Chemical Industry, 1950, pp. 298-304, 69.

Gault, et al., "Chlorination of Chloroform", Comptes Rendus Des Seances De L'Academie des Sciences, 1924, pp. 467-469, 179.

Gerding, et al., "Raman Spectra of aliphatic chlorine compounds: chloroethenes an chloropropenes", Recueil Jan. 1, 1955, pp. 957-975, 74.

Hatch, et al., "Allylic Chlorides. XV. Preparation and Properties of the 1,2,3Trichloropropenes", JACS, Jan. 5, 1952, pp. 123-126, 74.

Hatch, et al., "Allylic Chlorides. XVIII. Preparation and Properties of 1,1,3-tricholoro-2-fluoro-1-propene and 1,1,2,3-tetrachloro-1-propene", JACS, Jul. 5, 1952, pp. 3328-3330, 74(13).

Herzfelder, "Substitution in the Aliphatic Series", Berichte Der Deutschen Chemischen Gesellschaft, May-Aug. 1893, pp. 1257-1261, 26(2).

Huaping, et al., "Procress in Synthesis of 1,1,1,3-tetrachloropropane", Guangzhou Chemicals, 2011, , pp. 41-42, 39 (5).

Ivanov, et al., "Metal phthalocyanine-Catalyzed Addition of polychlorine-Containing Organic Compounds to C=C Bonds", Russian Chemical Bulletin, International Edition, Nov. 2009, pp. 2393-2396, 58(11).

Kang, et al., "Kinetics of Synthesis of 1,1,1,3,3-pentachlorobutane Catalyzed by Fe—FeCl3", Chemical Research and Application, Jun. 2011, pp. 657-660, 23(6).

Kharasch, et al., "Chlorinations with Sulfuryl Chloride.I. The Peroxide-Catalyzed Chlorination of Hydrocarbons", JAGS, 1939, pp. 2142-2150, 61.

Khusnutdinov, et al., "CCl4 Attachment to Olefins Catalyzed by Chromium and Ruthenium Complexes. Impact of Water as a Nucleophilic Admixture", Oil Chemistry, 2009, pp. 349-356, vol. 4.

Kruper, et al., "Synthesis of alpha-Halocinnamate Esters via Solvolytic Rearrangement of Trichloroallyl Alcohols", J Org Chem, 1991, pp. 3323-3329, 56.

Leitch, "Organic Deuterium Compounds: V. The chlorination of propyne and propyne D-4", Canadian Journal of Chemistry, Apr. 1, 1953, pp. 385-386, 30(4).

Levanova, et al., "Cholorination of Chloroolefins C3-C4", Doklady Chemistry, vol. 386, No. 4, 2002, 496-498.

Levanova, et al., "Thermocatalytic Reactions of Bromochloropropanes", Russian Journal of Physical Chemistry, Jan. 1, 1983, pp. 1142-1146, 57.

McBee, et al., "Utilization of Polychloropropanes and Hexachloroethane", Industrial and Engineering Chemistry,Feb. 1, 1941, pp. 176-181, 33(2).

Mouneyrat, "Effect of Chlorine on Propyl Chloride in the Presence of Anhydrous Aluminum Chloride", Bulletin de la Societe chimique de france, Societe francaise de chimie, Jan. 1, 1899, pp. 616-623, 21(3).

Munoz-Molina, et al., "An Efficient, Selective and Reducing Agent-Free Copper Catalyst for the Atom-Transfer Radical Addition of Halo Compounds to Activated Olefins", Inorg. Chem., 2010, pp. 643-645, 49.

Nair, et al., "Atom Transfer Radical Addition (ATRA) of Carbon Tetrachloride and Chlorinated Esters to Various Olefins Catalyzed by CP/Ru(PPh3)(PR3)CI Complexes", Inorganica Chimica Acta, 2012, pp. 96-103, 380.

Nguyen, et al., "Condensation de chloroforme avec des olefins fluorees en milieu basique", Journal of Fluorine Chemistry, Dec. 1, 1991, pp. 241-248, 55(3).

Nikishin, et al., "Reactions of Methanol and Ethanol with Tetrachloroethylene", Izvestiya Akademii Nauk SSSR, Seriya Khimicheskaya, Dec. 1966, pp. 2188-2192, 12.

Ochi, et al., "Preparation of Chloropropenes by Photochemical Dehydrochlorination of 1,2-Dichloropropane", Chemical Abstracts, Jul. 17, 1989, p. 574, 111(3).

Pozdnev, et al., "Chlorination of chloroform and the conversion of methylene chloride manufacture still residues", Khim., Khim. Tekhnol., 1970, 70(4).

Rotshtein, et al., "Isomer Distribution on Chlorination of Chloropropanes", Z. Organicheskoi Khimii, 1966, pp. 1539-1542, 2(9).

(56) References Cited

OTHER PUBLICATIONS

Semenov, "Selectivity of Photochemical Chlorination of Chloromethane in the Liquid Phase", Prikladnei Khimii, 1985, pp. 840-845, 58(4).

Shelton, et al., "Addition of Halogens and Halogen Compounds to Allylic Chlorides. I. Addition of Hydrogen Halides", Journal of Organic Chemistry, 1958, pp. 1876-1880, 23.

Skell, et al., "Reactions of BrCl with alkyl radicals", Tetrahedron letters, 1986 pp. 5181-5184, 27(43).

Skell, et al., "Selectivities of pi and sigma succinimidyl radicals in substitution and addition reactions, Response to Walling, WI-Taliawi and Zhao", JACS, Jul. 1, 1983, pp. 5125-5131, 105(15).

Stevens, "Some New Cyclopropanes with a Note on the Exterior Valence Angles of Cyclopropane", JACS, Vo. 68, No. 4, 1945, 620-622.

Tanuma, et al., "Partially Fluorinated Metal Oxide Catalysts for a Friedel-Crafts-type Reaction of Dichlorofluoromethane with Tetrafluoroethylene", Catal. Lett, 2010, pp. 77-82, 136.

Tobey, et al., "Pentachlorocyclopropane", Journal of the American Chemical Society, Jun. 1, 1996, pp. 2478-2481, 88 (11).

Urry, et al., "Free Radical Reactions of Diazomethane with Reactive Bromopolychloroalkane", JACS, May 5, 1964, pp. 1815-1819, 86(9.

Wang Chin-Hsien, "Elimination Reactions of polyhalopropanes under emulsion catalytic conditions to give Halopropenes", Synthesis, Jan. 1, 1982, pp. 494-496, 1982(6).

Zhao, et al., "Research Progress on Preparation Technology of 1,1,2,3-Tetrachloropropene", Zhejiang Chemical Industry, 2010, pp. 8-10, 41(6).

Zheng, et al., "Preparation of the low GWP alternative 1,3,3,3-tetrafluoropropene", Zhejiang Huagong, 2010, pp. 5-7, 41(3).

* cited by examiner

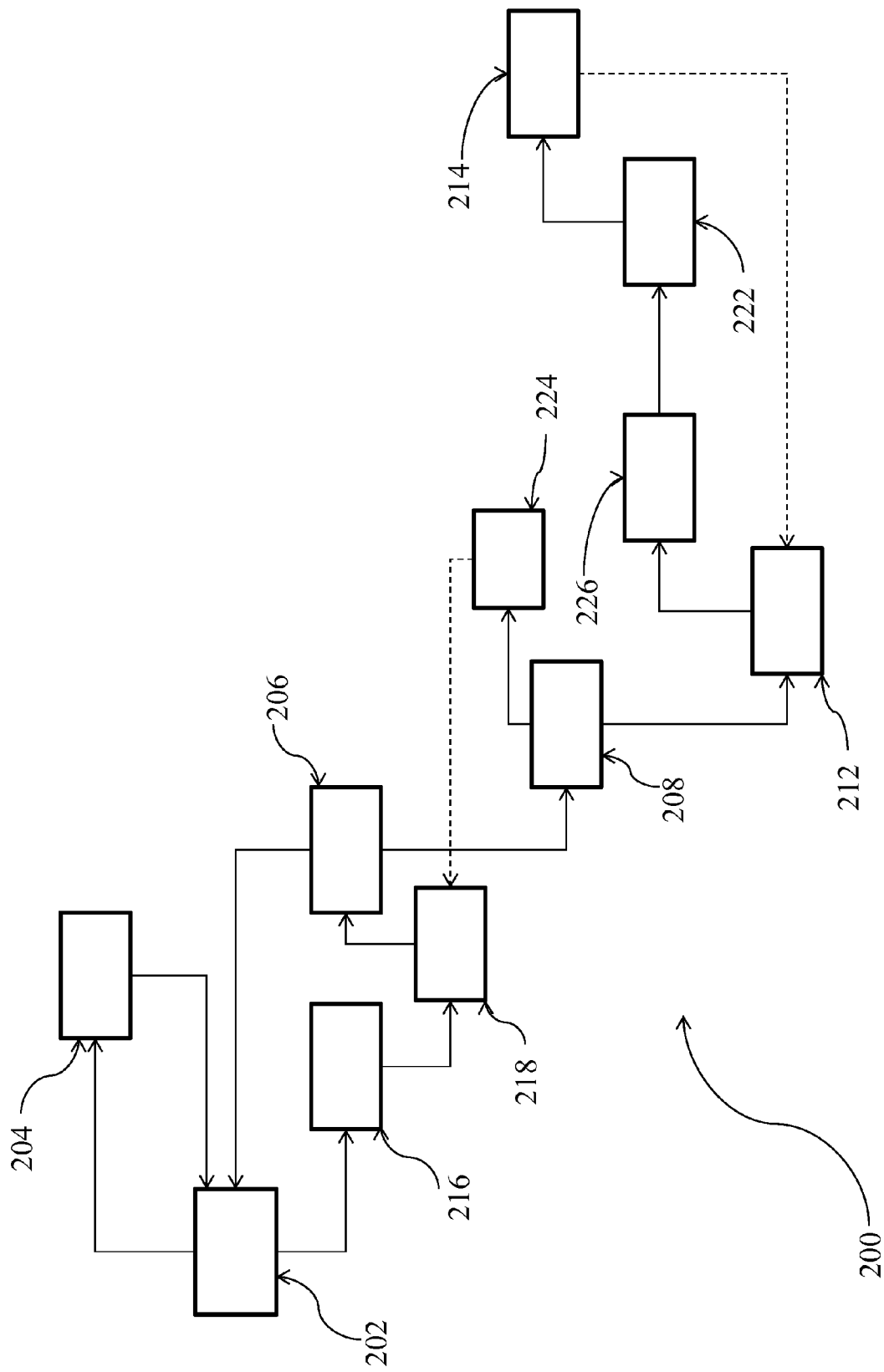

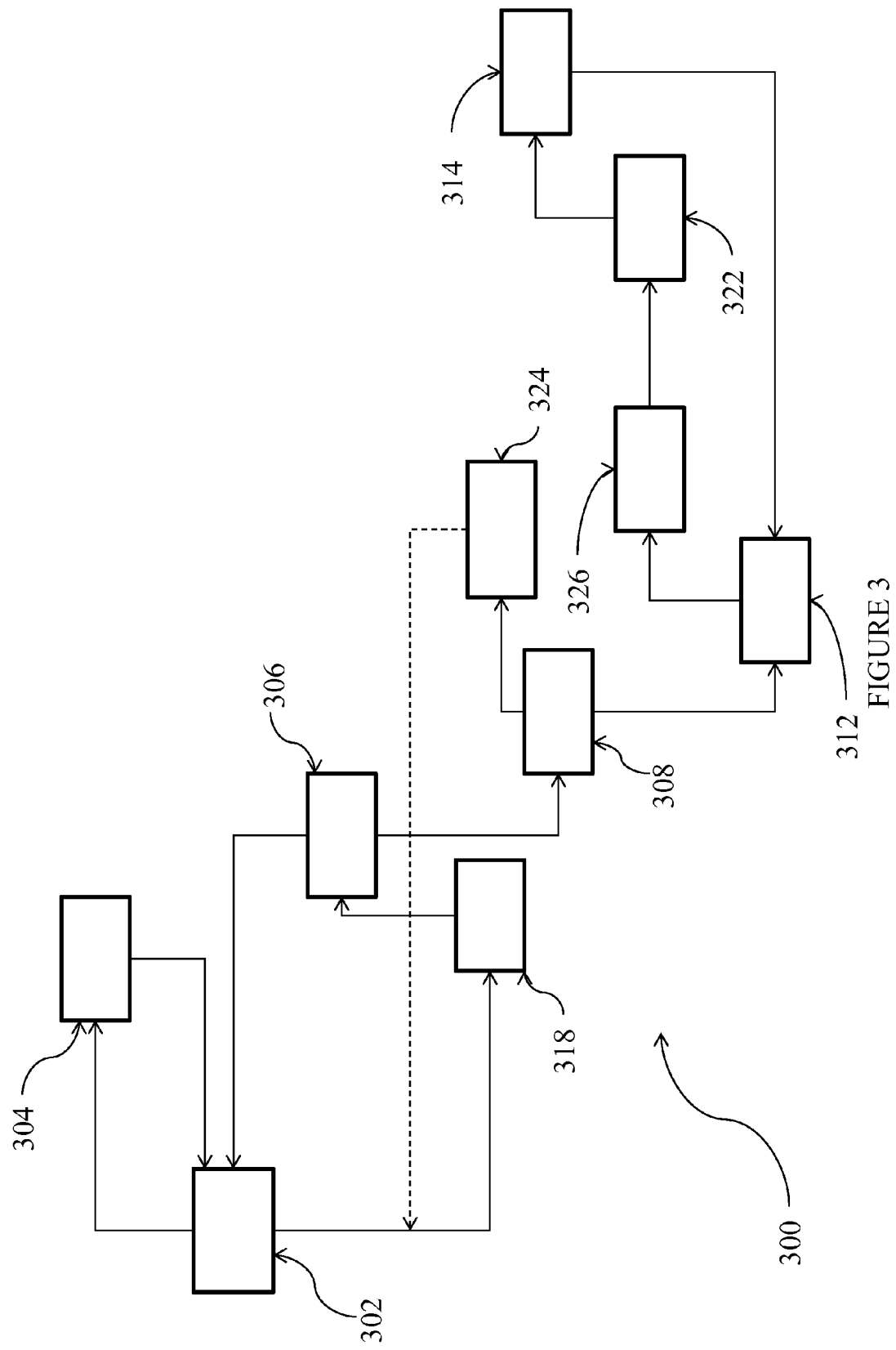

12
PROCESS FOR THE PRODUCTION OF CHLORINATED PROPENES

This application is a 371 of PCT/US2013/075909, filed on Dec. 18, 2013.

FIELD

The present invention relates to processes for the production of chlorinated propenes.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser, or no, detrimental impact on the ozone layer and their much lower GWP as compared to HFC's. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene or 1,3,3,3-tetrafluoroprop-1-ene, may typically be produced utilizing feedstocks of chlorocarbons, and in particular, chlorinated propenes, which may also find use as feedstocks for the manufacture of polyurethane blowing agents, biocides and polymers.

Unfortunately, many chlorinated propenes may have limited commercial availability, and/or may only be available at prohibitively high cost. This may be due at least in part to the fact that conventional processes for their manufacture may require the use of starting materials that are prohibitively expensive. Although alternative starting materials have been developed, processes using them may result in the formation of intermediates that are not amenable to the process conditions desirably or necessarily utilized to convert these new starting materials most efficiently to the desired chlorinated propene.

It would thus be desirable to provide improved processes for the large capacity and/or continuous production of chlorocarbon precursors useful as feedstocks in the synthesis of refrigerants and other commercial products. More particularly, such processes would provide an improvement over the current state of the art if they were less costly in starting materials, processing time, and/or capital costs required to implement and maintain the process. The use of processing conditions or steps that can remove or make use of intermediates typically recalcitrant to useful conversion would render such processes even more advantageous.

BRIEF DESCRIPTION

The present invention provides efficient processes for the production of chlorinated propenes. Advantageously, the processes make use of 1,2-dichloropropane, a by-product in the production of propylene chlorohydrin, as a low cost starting material. The selectivity of the process is enhanced over conventional chlorination processes by employing an ionic chlorination step and removing intermediates not amenable to the ionic chlorination from the product stream. Or, the ionic chlorination product stream may be subjected to a dehydrochlorination step using a basic chemical to convert any such intermediates into species more reactive toward further ionic chlorination. In this way, recycle of intermediates not amenable to ionic chlorination reactions is reduced or avoided, as is the buildup of these intermediates within the process. Higher yield and/or purity of desired chlorinated propenes can thus be seen, as compared to processes wherein these intermediates are recycled to the ionic chlorination reactor.

In one aspect, the present invention provides a process for the production of chlorinated propenes from one or more chlorinated propenes. The process utilizes a feedstream comprising 1,2-dichloropropane and subjects the same to an ionic chlorination step, which may be conducted in the presence of an ionic chlorination catalyst comprising a Lewis acid, such as aluminum chloride, ferric chloride, iodine, sulphur, iron, antimony pentachloride, boron trichloride, one or more lanthanum halides, and one or more metal triflates, or a combination of these.

After optionally quenching the ionic chlorination catalyst and drying the ionic chlorination product stream, at least a portion of any 1,2,3-trichloropropane, either alone or in combination with 1,2,2,3tetrachloropropane, is removed from the product stream or subjected to a dehydrochlorination step using a basic chemical. If the 1,2,3-trichloropropane, alone or with 1,2,2,3-tetrachloropropane is desirably removed from the process, it may be removed in whole or in part.

Or, a stream comprising the 1,2,3-trichloropropane, and possibly 1,2,2,3-tetrachloropropane may be dehydrochlorinated in the presence of a chemical base so that at least a portion of any 1,2,3-trichloropropane and/or 1,2,2,3-tetrachlopropane is cracked to provide a product stream comprising the chloropropene derivatives thereof. The chloropropenes from the basic chemical dehydrochlorination product stream are subjected to a further chlorination step, e.g., as by recycling to the first ionic chlorination step or by chlorination under the same or different conditions in an additional chlorination step/reactor, to provide a product stream comprising tetra- and pentachloropropanes. Any additional chlorination steps may be conducted in the presence of free radical initiators, such as those comprising chlorine, peroxide or azo group containing compounds, UV light, or combinations of these.

The pentachloropropanes produced by the basic chemical dehydrochlorination may be subjected to a further dehydrochlorination step or steps, which may be conducted either in the presence of a chemical base, or may be conducted catalytically. Catalytic dehydrochlorinations may advantageously be conducted in the presence of one or more Lewis acid catalysts, such as aluminum chloride, ferric chloride, iodine, sulphur, iron, antimony pentachloride, boron trichloride, one or more lanthanum halides, and one or more metal triflates, or a combination of these.

Any chlorinating agent may be used in the chlorination steps of the process, and suitable examples include sulfuryl chloride, chlorine or combinations of these. And, any additional chlorinations performed in the process may also be conducted in the presence or absence of an ionic chlorination catalyst, and may advantageously be conducted in the same reactor as the first ionic chlorination, if so desired. In other embodiments, any additional chlorinations may be conducted in a reactor separate from that used to carry out the ionic chlorination and may be carried out in the presence of one or more free radical initiators.

The advantages provided by the present processes may be carried forward by utilizing the chlorinated and/or fluorinated propenes to produce further downstream products, such as, e.g., 2,3,3,3-tetrafluoroprop-1-ene or 1,3,3,3-tetrafluoroprop-1-ene.

DESCRIPTION OF THE FIGURES

FIG. 2 shows a schematic representation of a process according to a further embodiment;
and
FIG. 3 shows a schematic representation of a process according to a further embodiment.

DETAILED DESCRIPTION

Figure 1:
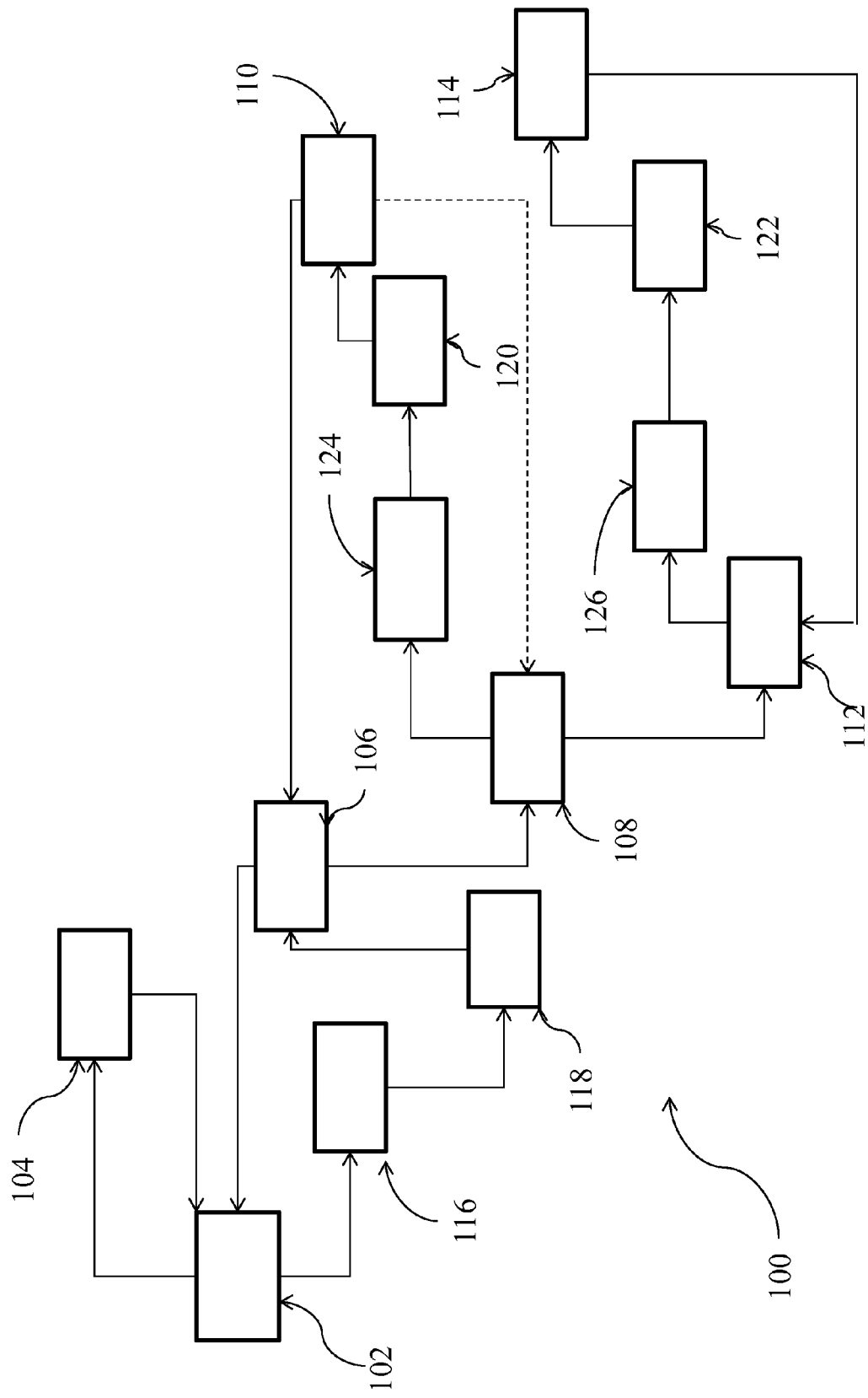
FIG. 1 shows a schematic representation of a process according to one embodiment.

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

In some instances, "PDC" may be used as an abbreviation for 1,2-dichloropropane and "TCPE" may be used as an abbreviation for 1,1,2,3-tetrachloropropene. The terms "cracking" and "dehydrochlorination" are used interchangeably to refer to the same type of reaction, i.e., one resulting in the creation of a double bond typically via the removal of a hydrogen and a chlorine atom from adjacent carbon atoms in chlorinated hydrocarbon reagents.

The present invention provides efficient processes for the production of chlorinated propenes. The present processes comprise conducting a first ionic chlorination on a feedstream comprising PDC. The use of PDC, a byproduct in many chlorohydrin processes, as a starting material is economically more attractive than disposing of it via incineration, as may be done in connection with some conventional chlorohydrin processes. Furthermore, those of ordinary skill in the art would not typically turn to PDC as a starting material in a process for the production of chlorinated propenes. This is at least because PDC, when subjected to many conventional process steps used in such processes, can form undesirable pentachloropropane isomers that are not easily reacted to provide the desired product.

Any ionic chlorination catalyst may be used in the ionic chlorination step of the present process. Exemplary ionic chlorination catalysts include, but are not limited to, aluminum chloride, ferric chloride ($FeCl_3$) and other iron containing compounds, iodine, sulfur, antimony pentachloride ($SbCl_5$), boron trichloride ($BCl_3$), lanthanum halides, metal triflates, and combinations thereof.

At least a portion of any tri- or tetrachlorinated propanes produced by the ionic chlorination that are not amenable to ionic chlorination conditions are desirably either removed from the process, or subjected to a dehydrochlorination step using a basic chemical. That is, the ionic chlorination of PDC may result in the formation of 10% or more 1,2,3-trichloropropane which is not particularly amenable to, and may even be considered to be substantially inert to, ionic chlorination. As a result, any amounts of 1,2,3-trichloropropane present in product streams that would desirably be chlorinated under ionic chlorination conditions, via recycling to the ionic chlorination reactor used in the first ionic chlorination step, may buildup in the system. Such a buildup may result in a loss of process capacity, and may ultimately necessitate shutting down the process to remove the 1,2,3-trichloropropane thus rendering the process uneconomical.

1,2,2,3-tetrachloropropane has a boiling point close to the boiling point 1,2,3-trichloropropane. As a result, separation techniques effective to remove 1,2,3-trichloropropane may result in the removal of at least a portion of any 1,2,2,3-tetrachloropropane within the same product stream. Unconverted 1,2,2,3-tetrachloropropane can also be difficult and expensive to remove from the final TCPE product. And so, at least a portion of any 1,2,2,3-tetrachloropropane produced by the process may also be removed from the process, or dehydrochlorinated along with, or separate from, the 1,2,3-trichloropropane.

In some embodiments of the process, at least a portion of any 1,2,3-trichloropropane and/or 1,2,2,3-tetrachloropropane produced by the ionic chlorination of PDC are removed from the process. Or, substantially all of any 1,2,3-trichloropropane and/or 1,2,2,3-tetrachloropropane produced by the ionic chlorination of PDC may be removed from the process. Combinations of these are also envisioned, i.e., in some embodiments, the 1,2,3-trichloropropane can be removed in whole or in part, either alone or in combination with partial or total removal of 1,2,2,3-tetrachloropropane.

While the separation and removal of either or both 1,2,3-trichloropropane and/or 1,2,2,3-tetrachloropropane may result in the removal of desirable chloropropane isomers thereby potentially reducing yield to the desired chlorinated propene, it may, more importantly, enable the process to run substantially continuously as compared to processes wherein no amount of 1,2,3-trichloropropane or 1,2,2,3-tetrachloropropane are removed.

In other embodiments of the process, at least a portion of any amount of 1,2,3-trichloropropane and/or 1,2,2,3-tetrachloropropane generated by the ionic chlorination step may be dehydrochlorinated, in the presence of a chemical base, to provide a product stream comprising the chloropropene derivatives thereof. These derivatives may then be chlorinated, e.g., via recycle of the chemical base dehydrochlorination product stream to the first ionic chlorination reactor, or provision thereof to an additional reactor, operated at the same, or different conditions. In such embodiments, higher yield is expected since the chlorination of the dehydrochlorination products of 1,2,2,3-tetrachloropropane will produce desirable pentachloropropane isomers.

Because at least a portion of any tri- or tetrachloropropane isomers not amenable to ionic chlorination are removed from the process, or dehydrochlorinated to form chlorinated propenes more amenable to ionic chlorination conditions, all chlorinations of the process may be conducted ionically, and may further advantageously be conducted in the same chlorination reactor. The expenditure associated with an additional chlorination reactor may thus be avoided, as can the utility costs associated with operating the same. However, use of the same reactor is not required to see the benefits of chlorinating the propene intermediates, as doing so is expected to result in a higher yield of desirable pentachloropropane isomers that are more easily converted to the desired end product.

The dehydrochlorination of the ionic chlorination stream is desirably done using a chemical base since 1,2,3-trichloropropane is practically inert to ionic dehydrochlorination. Liquid phase dehydrochlorination reactions using a chemical base such as caustic soda, potassium hydroxide, calcium hydroxide or a combination of these, can provide cost savings since evaporation of reactants is not required. The lower reaction temperatures used in liquid phase reactions may also result in lower fouling rates than the higher temperatures used in connection with gas phase reactions, and so reactor lifetimes may also be optimized when at least one liquid phase dehydrochlorination is utilized.

Many chemical bases are known in the art to be useful for liquid dehydrochlorinations, and any of these can be used. For example, suitable bases include, but are not limited to, alkali metal hydroxides, such as sodium hydroxide, potassium hydroxide, calcium hydroxide; alkali metal carbonates such as sodium carbonate; lithium, rubidium, and cesium or combinations of these. Phase transfer catalysts such as quaternary ammonium and quaternary phosphonium salts (e.g., tetrabutylammonium chloride, benzyltrimethylammonium chloride or hexadecyltributylphosphonium bromide) can also be added to improve the dehydrochlorination reaction rate with these chemical bases.

Other dehydrochlorination steps desirably carried out within the process can be carried out using a chemical base, or, may be carried out catalytically. In the case of the latter, anhydrous HCl can be recovered. Anhydrous HCl is of greater value than the sodium chloride that is produced as byproduct(s) of the chemical base cracking step(s). And so, in some embodiments, the process results in the production of a secondary product that may either be sold or used as a feedstock for other processes, e.g., ethylene oxychlorination to produce ethylene dichloride. If the use of catalysts is desired, suitable dehydrochlorination catalysts include, but are not limited to, ferric chloride ($FeCl_3$) or $AlCl_3$.

The present process makes use of a feedstock comprising 1,2-dichloropropane to produce the desired chlorinated propenes. The process feedstock may also comprise trichloropropane, or other chlorinated alkanes, if desired. And, the one or more components of the feedstock may be generated within or upstream of the process, if desired, e.g., as a byproduct in a chlorohydrin process.

Any chlorinated propene may be produced using the present method, although those with 3-4 chlorine atoms are more commercially viable, and production of the same may thus be preferred. In some embodiments, the process may be used in the production of 1,1,2,3-tetrachloropropene, which is highly sought after as a feedstock for refrigerants, polymers, biocides, etc.

If additional chlorination steps are carried out, they may be conducted in the presence of ionic chlorination catalysts in the same reactor, or, may be conducted in a separate reactor in the presence of one or more free radical initiators. Free radical initiators may typically comprise one or more chlorine, peroxide or azo-(R—N=N—R') groups and/or exhibit reactor phase mobility/activity. As used herein, the phrase "reactor phase mobility/activity" means that a substantial amount of the initiator is available for generating free radicals of sufficient energy which can initiate and propagate effective turnover of the product, the chlorinated and/or fluorinated propene(s), within the design limitations of the reactor.

Such free radical initiators are well known to those skilled in the art and have been reviewed, e.g., in "Aspects of some initiation and propagation processes," Bamford, Clement H. Univ. Liverpool, Liverpool, UK., Pure and Applied Chemistry, (1967), 15(3-4), 333-48 and Sheppard, C. S.; Mageli, O. L. "Peroxides and peroxy compounds, organic," Kirk-Othmer Encycl. Chem. Technol., 3rd Ed. (1982), 17, 27-90.

Examples of suitable free radical initiators comprising chlorine include, but are not limited to carbon tetrachloride, hexachloroacetone, chloroform, hexachloroethane, phosgene, thionyl chloride, sulfuryl chloride, trichloromethylbenzene, perchlorinated alkylaryl functional groups, or organic and inorganic hypochlorites, including hypochlorous acid, and t-butylhypochlorite, methylhypochlorite, chlorinated amines (chloramine) and chlorinated amides or sulfonamides such as chloroamine-T®, and the like.

Examples of suitable free radical initiators comprising one or more peroxide groups include hydrogen peroxide, hypochlorous acid, aliphatic and aromatic peroxides or hydroperoxides, including di-t-butyl peroxide, benzoyl peroxide, cumyl peroxide and the like. Diperoxides offer an advantage of not being able to propagate competitive processes (e.g., the free radical chlorination of PDC to TCP (and its isomers) and tetrachloropropanes). In addition, compounds containing azo groups, such as azobisisobutyronitrile (AIBN) or 1,1'-azobis(cyclohexanecarbonitrile (ABCN), may also be used. Combinations of any of these may also be utilized.

The reactor zone may also be subjected to pulse laser or continuous UV/visible light sources at a wavelength suitable for inducing photolysis of the free radical initiator, as taught by Breslow, R. in *Organic Reaction Mechanisms* W. A. Benjamin Pub, New York p 223-224. Wavelengths from 300 to 700 nm of the light source are sufficient to dissociate commercially available radical initiators. Such light sources include, e.g., Hanovia UV discharge lamps, sunlamps or even pulsed laser beams of appropriate wavelength or energy which are configured to irradiate the chlorination reactor. Alternatively, chloropropyl radicals may be generated from microwave discharge into a bromochloromethane feedsource introduced to the reactor as taught by Bailleux et al., in Journal of Molecular Spectroscopy, 2005, vol. 229, pp. 140-144.

Any or all of the catalysts utilized in the process can be provided either in bulk or in connection with a substrate, such as activated carbon, graphite, silica, alumina, zeolites, fluorinated graphite and fluorinated alumina. Whatever the desired catalyst (if any), or format thereof, those of ordinary skill in the art are well aware of methods of determining the appropriate format and method of introduction thereof. For example, many catalysts are typically introduced into the reactor zone as a separate feed, or in solution with other reactants.

The amount of any free radical initiator, ionic chlorination and/or dehydrochlorination catalyst utilized will depend upon the particular catalyst/initiator chosen as well as the other reaction conditions. Generally speaking, in those embodiments of the invention wherein the utilization of a catalyst/initiator is desired, enough of the catalyst/initiator should be utilized to provide some improvement to reaction process conditions (e.g., a reduction in required temperature) or realized products, but yet not be more than will provide any additional benefit, if only for reasons of economic practicality.

For purposes of illustration only then, it is expected, that useful concentrations of an ionic chlorination catalyst will range from 0.001% to 20% by weight, or from 0.01% to 10%, or from 0.1% to 5 wt. %, inclusive of all subranges therebetween. Useful concentrations of a free radical initiator will range from 0.001% to 20% by weight, or from 0.01% to 10%, or from 0.1% to 5 wt. %. If a dehydrochlorination catalyst is utilized for one or more dehydrochlorination steps, useful concentrations may range from 0.01 wt. % to 5 wt. %, or from 0.05 wt. % to 2 wt. % at temperatures of from 70° C. to 200° C. If a chemical base is utilized for one or more dehydrochlorinations, useful concentrations of these will range from 0.01 to 20 grmole/L, or from 0.1 grmole/L to 15 grmole/L, or from 1 grmole/L to 10 grmole/L, inclusive of all subranges therebetween. Relative concentrations of each catalyst/base are given relative to the feed, e.g., 1,2-dichloropropane.

The chlorination steps of the process may be carried out using any chlorination agent, and several of these are known in the art. For example, suitable chlorination agents include, but are not limited to chlorine, and/or sulfuryl chloride ($SO_2Cl_2$). Combinations of chlorinating agents may also be used. Either or both $Cl_2$ and sulfuryl chloride may be particularly effective when aided by the use of the aforementioned ionic chlorination catalysts.

In additional embodiments, one or more reaction conditions of the process may be optimized, in order to provide even further advantages, i.e., improvements in selectivity, conversion or production of reaction by-products. In certain embodiments, multiple reaction conditions are optimized and even further improvements in selectivity, conversion and production of reaction by-products produced can be seen.

Reaction conditions of the process that may be optimized include any reaction condition conveniently adjusted, e.g., that may be adjusted via utilization of equipment and/or materials already present in the manufacturing footprint, or that may be obtained at low resource cost. Examples of such conditions may include, but are not limited to, adjustments to temperature, pressure, flow rates, molar ratios of reactants, etc.

That being said, the particular conditions employed at each step described herein are not critical, and are readily determined by those of ordinary skill in the art. What is important is that a feedstream comprising 1,2-dichloropropane is used as a starting material and subjected to an ionic chlorination step, and that at least a portion of any 1,2,3-trichloropropane and/or 1,2,2,3-tetrachloropropane produced by the ionic chlorination step is removed from the process, or reacted to produce tetra-, pentachloropropane and/or chloropropene intermediates more amenable to ionic chlorination conditions. Those of ordinary skill in the art will readily be able to determine suitable equipment for each step, as well as the particular conditions at which the chlorination, dehydrochlorination, separation, drying, and isomerization steps may be conducted.

In one exemplary embodiment, PDC is fed to a liquid phase reactor, e.g., such as a batch or continuous stirred tank autoclave reactor with an internal cooling coil or an external heat exchanger. A shell and multitube exchanger followed by vapor liquid disengagement tank or vessel can also be used. Suitable reaction conditions include, e.g., temperatures of from ambient temperature (e.g., 20° C.) to 200° C., or from 30° C. to 150° C., or from 40° C. to 120° C. or from 50° C. to 100° C. Ambient pressure may be used, or pressures of from 100 kPa to 1000 kPa, or from 100 kPa to 500 kPa, or from 100 kPa to 300 kPa. At such conditions, and using one or more ionic chlorination catalysts, PDC is chlorinated to tri-, tetra-, and pentachlorinated propanes at conversions of greater than 60%, or 70%, or 80%, or 85%, or even up to 90% can be seen.

The process may be carried out neat, i.e., in the absence of solvent, or, one or more solvents may be provided to the chlorination reactor, and may be provided as feedstock, or, recycled from one or more separation columns operably disposed to receive streams from the chlorination reactor. For example, unconverted PDC, trichloropropane, dichloropropene, and trichloropropene intermediates may be recycled back to the chlorination reactor from one separation column, and/or the chlorination reactor may be provided with a feedstock of any appropriate solvent for chlorination reactions, such as, e.g., carbon tetrachloride, sulfuryl chloride, 1,1,2,3,3-pentachloropropane, 1,1,2,2,3,3-hexachloropropane, other hexachloropropane isomers, or a combination of these.

The overhead vapor from the chlorination reactor, is cooled, condensed and fed to a first separation column. This column is operated at conditions effective to provide anhydrous HCl to an overhead line thereof and chlorine through a bottom recycle line. More particularly, the top temperature of such a column can typically be set below 0° C. or more preferably, can be set at a temperature of from −70° C. to −10° C. The bottom temperature of this column is desirably set at from 10° C. to 150° C., or from 30° C. to 100° C., with the exact temperature dependent to some degree on the bottom mixture composition. The pressure of this column is desirably set above 200 kPa or preferably, from 500 kPa to 2000 kPa, or more preferably from 500 kPa to 1000 kPa. The bottom stream of a column operated at such conditions would be expected to contain excess chlorine, unreacted PDC and monochloropropene intermediates, while the overhead stream would be expected to comprise anhydrous HCl.

In some embodiments, the liquid product stream from the chlorination reactor may be fed to a second separation column operated at conditions effective to recover an overhead stream comprising unreacted PDC and 1,1,2-trichloropropane. This stream is then recycled to the ionic chlorination reactor. The bottom product can then be provided to another separation unit.

In another embodiment, a stream comprising 1,2,3-trichloropropane from the ionic chlorination product is separated from the other products comprising tetra and pentachlorinated propanes in a third separation unit. The overhead stream from this separation column, comprising 1,2,3-trichloropropane, is removed from the process, while the bottom stream, expected to comprise tetra- and pentachloropropanes and heavier by-products, such as isomers of hexachloropropanes, may be provided to a further separation column.

This fourth separation column separates the desirable pentachloropropanes, i.e., 1,1,2,2,3-pentachloropropane and 1,1,1,2,2-pentachloropropane, from the less desirable 1,1,2,3,3-pentachloropropane and heavier components, which are purged as a bottom stream. The overhead stream comprising 1,1,2,2,3-pentachloropropane, 1,1,1,2,3-pentachloropropane, and 1,1,1,2,2-pentachloropropane is then provided to a reactor where it is dehydrochlorinated using chemical base to provide 2,3,3,3-tetrachloropropene and 1,1,2,3-tetrachloropropene. More specifically, dehydrochlorination reactor may typically be a batch or a continuous stirred tank reactor. The mixing can be done, e.g., by mechanical or jet mixing of feed streams. Those of ordinary skill in the art are readily able to determine the appropriate conditions at which to run a dehydrochlorination reactor in order to conduct the aforementioned dehydrochlorination.

The reaction stream from the dehydrochlorination reactor may optionally be provided to a drying column, and the dried stream therefrom provided to a further reactor to isomerize the 2,3,3,3-tetrachloropropene to 1,1,2,3-tetrachloropropene under the appropriate conditions. For example, catalysts may be utilized to assist in the isomerization, in which case, suitable catalysts include, but are not limited to (i) siliceous granules having a polar surface including kaolinite, bentonite, and attapulgite; (ii) other mineral salts of silica such as saponite or quartz; or (iii) siliceous non-mineral substance such as silica gel, fumed silica, and glass, or combinations of any of these. Suitable conditions for drying columns for such reaction streams are also known to those of ordinary skill in the art, as evidenced by U.S. Pat. No. 3,926,758.

In other embodiments, the product stream from the ionic chlorination reactor may be provided to one or more separation units effective to provide a product stream comprising dichloropropanes and 1,1,2-trichloropropane that may be recycled to the ionic chlorination reactor, and another comprising 1,2,3-trichloropropane and tetrachloropropanes that may be provided to a dehydrochlorination reactor charged with a chemical base. The chemical base dehydrochlorination reactor would provide a product stream comprising di- and trichloropropenes that may ultimately be recycled to the ionic chlorination reactor.

A schematic illustration of such a process is shown in FIG. 1. As shown in FIG. 1, process 100 would make use of chlorination reactor 102, separation columns 104, 106, 108, 110, 112 and 114, quench unit 116, driers 118, 120 and 122, and dehydrochlorination reactors 124 and 126. In operation, 1,2-dichloropropane, one or more ionic chlorination catalysts and the desired chlorination agent (e.g., chlorine, $SO_2Cl_2$, or combinations of these) are fed, or otherwise provided, to chlorination reactor 102, which may be operated at any set of conditions operable to provide for the chlorination of PDC to tri-, tetra- and pentachlorinated propanes.

The overhead stream of chlorination reactor 102, comprising HCl, excess chlorination agent and unreacted PDC, is fed to separation column 104. The feed to the separation column is preferably totally condensed liquid at temperature −40° C. to 0° C. made by applying a fractionation method such as that described in U.S. Pat. No. 4,010,017. Separation column 104 is operated at conditions effective to provide anhydrous HCl through an overhead line and chlorine and PDC back to chlorination reactor 102.

The liquid bottom stream of reactor 102 is fed to quench unit 116. Quench unit may be a stirred tank reactor and will desirably be operated at conditions effective to convert the ionic chlorination catalyst to an inactive form thereof, i.e., quench unit may desirably be operated at temperatures of from 20° C. to 80° C. and atmospheric pressure or higher. The quenched stream from quench unit 116 is provided to drying unit 118, where it is dried and the hydroxylated ionic chlorination catalyst removed. The dried product stream, which may also comprise unreacted PDC, is provided to separation unit 106.

Separation unit 106 provides an overhead stream comprising PDC, 1,3-dichloropropane and 1,1,2-trichloropropane, which is recycled to chlorination reactor 102. The bottom stream of separation unit 106, comprising 1,2,3-trichloropropane and tetra- and pentachlorinated propanes is provided to separation unit 108. Separation unit 108 provides an overhead stream comprising 1,2,3-trichloropropane and 1,2,2,3-tetrachloropropanes, which is fed to chemical base dehydrochlorination reactor 124.

Chemical base dehydrochlorination reactor 124, which may typically be charged with caustic soda, potassium hydroxide, calcium hydroxide or a combination of these and operated at pressures of ambient to 400 kPa and temperatures of from 40° C. to 150° C., dehydrochlorinates the 1,2,3-trichloropropane, 1,2,2,3-tetrachloropropane, and other tetrachloropropanes to di- and trichloropropenes, and this product stream is fed to drying unit 120 for the removal of water and sodium chloride. The dried stream, comprising unreacted 1,2,3-trichloropropane and tetrachloropropanes in addition to the di- and trichloropropenes, is provided to separation unit 110. Separation unit 110 provides a bottoms stream comprising unreacted tri and tetrachloropropanes that may be recycled to separation unit 108 and an overhead stream comprising di- and trichloropropenes that may be recycled to separation unit 106. The di- and trichloropropenes together with the PDC and 1,1,2-trichloropropane are then recycled to ionic chlorination reactor 102.

Alternatively (not shown in FIG. 1), the product stream from drying unit 120 may also undergo further purification in a separation unit prior to recycling back to chlorination reactor 102. The bottom stream of separation unit 108, comprising pentachloropropanes and heavier secondary products, is provided to separation unit 112, where the pentachloropropane intermediates amenable to conversion, i.e., 1,1,2,2,3- and much smaller, if any, amounts of 1,1,1,2,2-pentachloropropane are provided as an overhead stream to dehydrochlorination reactor 126. The bottoms stream from separation unit 112, comprising hexachlorinated propanes and heavier secondary products, may be appropriately disposed of. Dehydrochlorination reactor 126 dehydrochlorinates the pentachloropropanes using one or more chemical bases to provide a product stream comprising TCPE, which may then be provided to drying unit 122, and the dried stream provided to separation unit 114. Separation unit 114 provides TCPE as an overhead stream and unreacted pentachlorinated propanes as a bottoms stream, which may be recycled to separation unit 112, if desired.

In some embodiments, the stream to dehydrochlorination reactor 126 may further comprise 1,1,2,3-tetrachloropropane. In such embodiments, it may be desirable to include an additional separation unit (not shown) upstream of separation unit 114 to separate any trichloropropenes and return them to chlorination reactor 102. In other embodiments, a third dehydrochlorination reactor may be used (not shown)

to catalytically crack tetrachloropropanes and/or pentachloropropanes to produce chloropropenes and anhydrous HCl. This unit can be placed before or after the chemical base dehydrochlorination unit.

In process 100, 1,2,3-trichloropropane and 1,2,2,3-tetrachloropropropane produced by the initial ionic chlorination of PDC in chlorination reactor 102 are dehydrochlorinated in the presence of a chemical base to provide chloropropenes which are then recycled to chlorination reactor 102. By recycling the chloropropenes produced by the chemical base dehydrochlorination of 1,2,3-trichloropropane and 1,22,3-tetrachloropropane, rather than 1,2,3-trichloropropane, the buildup of 1,2,3-trichloropropane, largely resistant to ionic chlorination conditions, within the process is reduced or eliminated. Continuous operation of process 100 is thus provided.

One further exemplary process for the production of chlorinated propenes is schematically illustrated in FIG. 2. Process 200 makes use of chlorination reactor 202, separation columns 204, 206, 208, 212 and 214, quench unit 216, driers 218 and 222, and dehydrochlorination reactors 224 and 226.

Process 200 is similar to process 100, except that the product stream from dehydrochlorination reactor 224, comprising di- and trichloropropenes and tetrachloropropanes is recycled to drying unit 218, rather than provided to an additional drying unit (e.g., 120 in FIG. 1). Separation unit 206 then desirably acts to provide an overhead stream comprising di-, trichloropropenes, PDC and 1,1,2-trichloropropane to chlorination reactor 202. And so, process 200 requires one less drying unit (drying unit 120 in FIG. 1) and one less separation unit (separation unit 110 in FIG. 1) than process 100, while yet maintaining higher yield and purity to TCPE than conventional processes for the production thereof that do not comprise a chemical base dehydrochlorination step following an ionic chlorination. Process 200 otherwise operates identically to process 100, and is also capable of continuous operation.

A further exemplary process for the production of chlorinated propenes is schematically illustrated in FIG. 3. Process 300 makes use of chlorination reactor 302, separation columns 304, 306, 308, 312 and 314, driers 318 and 322, and dehydrochlorination reactors 324 and 326.

Process 300 is similar to process 100, except that the product stream from dehydrochlorination reactor 324, comprising di- and trichloropropenes and unconverted tri and tetrachloropropanes together with the aqueous byproduct is mixed with the product stream of reactor 302 before being fed to dryer 318. In this way, the product stream from dehydrochlorination reactor 324 is directly used as a catalyst quench, and the use of a quench unit (e.g., 116 in FIG. 1) is not necessary. Separation unit 306 then desirably acts to provide an overhead stream comprising di-, trichloropropenes, PDC and 1,1,2-trichloropropane to chlorination reactor 302. In sum, process 300 requires less equipment, i.e., no quench unit (116 in FIG. 1), one less drying unit (drying unit 120 in FIG. 1) and one less separation unit (separation unit 110 in FIG. 1) than process 100, while yet maintaining higher yield and purity to TCPE than conventional processes for the production thereof that do not comprise a chemical base dehydrochlorination step following an ionic chlorination. Process 300 otherwise operates identically to process 100, and is also capable of continuous operation.

The chlorinated propenes produced by the present process may typically be processed to provide further downstream products including hydrofluoroolefins, such as, for example, 1,3,3,3-tetrafluoroprop-1-ene (HFO-1234ze). Since the present invention provides an improved process for the production of chlorinated propenes, it is contemplated that the improvements provided will carry forward to provide improvements to these downstream processes and/or products. Improved methods for the production of hydrofluoroolefins, e.g., such as 2,3,3,3-tetrafluoroprop-1-ene (HFO-1234yf), are thus also provided herein.

The conversion of chlorinated propenes to provide hydrofluoroolefins may broadly comprise a single reaction or two or more reactions involving fluorination of a compound of the formula $C(X)_mCCl(Y)_n(C)(X)_m$ to at least one compound of the formula $CF_3CF=CHZ$, where each X, Y and Z is independently H, F, Cl, I or Br, each m is independently 1, 2 or 3 and n is 0 or 1. A more specific example might involve a multi-step process wherein a feedstock of a chlorinated propene is fluorinated in a catalyzed, gas phase reaction to form a compound such as 1-chloro-3,3,3-trifluoropropene (1233zd). The 1-chloro-3,3,3-trifluoropropene is then hydrofluorinated to give 1-chloro-2,3,3,3-tetrafluoropropane, which is then dehydrochlorinated to 2,3,3,3-tetrafluoroprop-1-ene or 1,3,3,3-tetrafluoroprop-1-ene via a catalyzed, gas phase reaction.

EXAMPLE 1

Ionic Chlorination of PDC

A 100 mL Parr reactor is charged with $AlCl_3$ (100 mg), $CH_2Cl_2$ (45 mL) and sealed. The shot tank is charged with PDC (1 mL) and $CH_2Cl_2$ (9 mL). The reactor is fully vented and pressured with $Cl_2$ (30% v/v in $N_2$) to 125 psig. $Cl_2$ flow is continued for 30 min and then turned off. The reactor is heated to 70° C. and the pressure readjusted to 125 psig. The PDC solution is then added (t=0) and samples are periodically taken. Table 1, below, shows the chloropropane distribution in mol % as a function of time. As shown by Table 1, 1,2,3-trichloropropane and 1,1,2,3-tetrachloropropane are relatively inert once they are produced initially from PDC chlorination. In contrast, the other tri- and tetrachloropropane intermediates undergo chlorination readily to pentachloropropane isomers and heavier byproducts.

TABLE 1

Product composition (in mole %) of PDC ionic chlorination using $AlCl_3$.

| | Time (min) | | | | | | |
|---|---|---|---|---|---|---|---|
| | 0 | 5 | 15 | 30 | 63 | 136 | 246 |
| | | | | mol % | | | |
| 1,2-dichloropropane | 100 | 0 | 0 | 0 | 0 | 0 | 0 |
| 112-trichloropropane | 0 | 73 | 60 | 41 | 19 | 3.5 | 0.48 |
| 123-trichloropropane | 0 | 15 | 15 | 15 | 16 | 15 | 15 |
| 1122-tetrachloropropane | 0 | 1.0 | 0.84 | 0.62 | 0.28 | 0.03 | 0 |
| 1123-tetrachloropropane | 0 | 1.8 | 2.5 | 3.3 | 4.5 | 6.0 | 6.0 |
| 1223-tetrachloropropane | 0 | 2.3 | 3.68 | 3.73 | 2.04 | 0.39 | 0.06 |
| 11223-pentachloropropane | 0 | 4.2 | 11 | 22 | 36 | 45 | 44 |
| 11122-pentachloropropane | 0 | 0.15 | 0.24 | 0.41 | 0.34 | 0.1 | 0 |
| 112233-hexachloropropane | 0 | 2.3 | 6.3 | 12 | 21 | 28 | 31 |
| 111223-hexachloropropane | 0 | 0 | 0.09 | 0.74 | 1.3 | 1.7 | 2.2 |
| 1112233-hexachloropropane | 0 | 0 | 0.18 | 0.25 | 0.56 | 0.72 | 0.86 |

EXAMPLE 2

Ionic Chlorination of PDC

A 100 mL Parr reactor is charged with $AlCl_3$ (100 mg), $I_2$ (20 mg) and $CH_2Cl_2$ (45 mL) and sealed. The shot tank is charged with PDC (1 mL) and $CH_2Cl_2$ (9 mL). The reactor is fully vented and pressured with $Cl_2$ (30% v/v in $N_2$) to 125 psig. $Cl_2$ flow is continued for 30 min and then turned off. The reactor is heated to 70° C. and the pressure readjusted to 135 psig. The PDC solution is then added (t=0) and samples are periodically taken. Table 2, below, shows the chloropropane distribution in mol % as a function of time.

As shown by Table 2, 1,2,3-trichloropropane and 1,1,2,3-tetrachloropropane are relatively inert once they are produced initially from PDC chlorination. In contrast, the other tri- and tetrachloropropane intermediates undergo chlorination readily to pentachloropropane isomers and heavier byproducts.

TABLE 2

Product composition (in mole %) of PDC ionic chlorination using $AlCl_3/I_2$.

| | sample 0 | sample 1 | sample 2 | sample 3 | sample 4 | sample 5 | sample 6 |
|---|---|---|---|---|---|---|---|
| | \multicolumn{7}{c}{Time (min)} | | | | | | |
| | 0 | 5 | 10 | 15 | 30 | 60 | 120 |
| | \multicolumn{7}{c}{mol %} | | | | | | |
| 1,2-dichloropropane | 100 | 0 | 0 | 0 | 0 | 0 | 0 |
| 1,1,2-trichloropropane | 0 | 77 | 70 | 63 | 44 | 26 | 12 |
| 1,2,3-trichloropropane | 0 | 15 | 14 | 14 | 15 | 11 | 14 |
| 1,1,2,2-tetrachloropropane | 0 | 1.3 | 1.1 | 1.0 | 0.79 | 0.39 | 0.17 |
| 1,1,2,3-tetrachloropropane | 0 | 0 | 1.3 | 1.5 | 1.8 | 4.6 | 4.2 |
| 1,2,2,3-tetrachloropropane | 0 | 2.4 | 4.0 | 4.6 | 5.1 | 3.2 | 1.5 |
| 1,1,2,2,3-pentachloropropane | 0 | 3.9 | 8.4 | 13 | 28 | 48 | 58 |
| 1,1,1,2,2-pentachloropropane | 0 | 0.077 | 0.21 | 0.38 | 0.62 | 0.49 | 0.29 |
| 1,1,2,2,3,3-hexachloropropane | 0 | 0.58 | 0.94 | 1.7 | 3.2 | 6.3 | 7.9 |
| 1,1,1,2,2,3-hexachloropropane | 0 | 0 | 0 | 0 | 1.3 | 0.2 | 1.8 |

EXAMPLE 3

Dehydrochlorination of a Mixture of 1,2,2,3-tetrachloropropane and 1,2,3-trichloropropane using a Chemical Base A flask equipped with a stir bar is charged with the phase transfer catalyst tetrabutylammonium chloride (20 mg) and 7 g of a mixture of 123-trichloropropane and 1223-tetrachloropropane (See Table 1, t=0 for composition). The mixture is flushed with $N_2$ and heated to 80° C. An aqueous solution of NaOH (9 mL, 5 N) is added dropwise over several minutes. The mixture is stirred vigorously at 80° C. and sampled after 1 and 3 h. Analysis by $^1H$ NMR spectroscopy indicates the following product composition (Table 3):

TABLE 3

| | Time (min) | | |
|---|---|---|---|
| | 0 | 60 | 180 |
| | \multicolumn{3}{c}{mol %} | | |
| 1,2,3-trichloropropane | 71 | 10 | 2 |
| 1,2,2,3-tetrachloropropane | 28 | 9 | 4 |
| 2,3-dichloropropene | 0 | 61 | 66 |
| cis/trans 1,2,3-trichloropropene | 0 | 20 | 28 |

EXAMPLE 4

Chlorination of a Mixture of 2,3-dichloropropene and 1,2,3-trichloroprene

A pressure reactor is charged with a mixture of di- and trichloropropenes (3.35 g) and the free radical initiator carbon tetrachloride (45 mL). Stirring (900 rpm) is initiated and the reactor is pressured with a chlorine/nitrogen mixture (30% $Cl_2$ in $N_2$ v/v) to a pressure of ~140 psig. The chlorine/nitrogen mixture is passed through the reactor at that pressure for about 30 minutes at 25° C. and a flow rate of 200 sccm. The mixture is then sampled and analyzed by 1H NMR spectroscopy which indicates that 2,3-dichloropropene and 1,2,3-trichloropropene are converted to 1,2,2,3-tetrachloropropane and 1,1,2,2,3-pentachloroprane, respectively with high selectivity. Analysis by $^1H$ NMR spectroscopy indicates the following product composition (Table 4):

TABLE 4

| | Time (min) | |
|---|---|---|
| | 0 | 30 |
| | \multicolumn{2}{c}{mol %} | |
| 2,3-dichloropropene | 66 | 5 |
| cis/trans 123-trichloropropene | 28 | 5 |
| 1,2,3-trichloropropane | 2 | 1 |
| 1,2,2,3-tetrachloropropane | 4 | 63 |
| 1,1,2,2,3-pentachloropropane | | 24 |
| other chloropropanes | | 2 |

This example shows that the products of the chlorination of di- and trichloropropenes are similar to those produced in the initial ionic chlorination reactor and these can be re-exposed to the reaction conditions to produce desired intermediates and/or products with high selectivity.

EXAMPLE 5

Chlorination of 2,3-chloropropene

A pressure reactor was charged with aluminum chloride (0.15 g) and the solvent methylene chloride (50 mL). The reactor was closed and pressure checked to 160 psig prior to initiating a flow of 30:70 $Cl_2:N_2$ gas (100 sccm) under constant stirring (800 rpm) and reactor pressure (150 psig). The reaction mixture was heated to 70° C. and then charged with 2,3-dichloropropene (10 mL,). The reaction was monitored by removing 1 mL aliquots at 15, 60, 80, and 160 minutes after the chloropropene addition. These aliquots were quenched with water and then analyzed by gas chromatography to determine the product composition, shown in Table 5, below.

TABLE 5

| | \multicolumn{5}{c}{Time (s)} | | | | |
|---|---|---|---|---|---|
| | 0 | 925 | 2065 | 4897 | 9366 |
| | | | Mol % | | |
| 2,3-dichloropropene | 100.0% | 43.7% | 9.4% | 0.0% | 0.0% |
| 1,1,2,2-tetrachloropropane | | 17.1% | 47.9% | 56.9% | 41.7% |
| 1,2,2,3-tetrachloropropane | 0 | 36.9% | 40.2% | 28.8% | 25.1% |
| 1,1,2,3-tetrachloropropane | 0 | 0.0% | 0.0% | 4.1% | 0.8% |
| 1,1,2,2,3-pentachloropropane | 0 | 1.0% | 1.4% | 10.2% | 21.4% |
| 1,1,2,2,3,3-hexachloropropane | 0 | 1.2% | 1.1% | 0.0% | 11.0% |

EXAMPLE 6

Chlorination of 2,3-chloropropene

A pressure vessel was charged with aluminum chloride (0.15 g), iodine (0.03 g), and methylene chloride solvent (50 mL). The reactor was closed and pressure checked to 160 psig prior to initiating a flow of 30:70 $Cl_2:N_2$ gas (100 sccm) under constant stirring (800 rpm) and reactor pressure (135 psig). The reaction mixture was heated to 70° C. and then charged with 2,3-dichloropropene (10 mL). The reaction was monitored by removing 1 mL aliquots at 15, 30, 90, and 150 minutes after the chloropropene addition. These aliquots were quenched with water and then analyzed by gas chromatography to determine the product composition, shown in Table 6, below.

TABLE 6

| | \multicolumn{5}{c}{Time (s)} | | | | |
|---|---|---|---|---|---|
| Substrate | 0 | 880 | 1785 | 5574 | 8922 |
| | | | Mol % | | |
| 2,3-dichloropropene | 100.0% | 64.9% | 39.5% | 0.0% | 0.0% |
| 1,2,2-trichloropropane | 0.0% | 17.8% | 28.0% | 8.4% | 0.0% |
| 1,2,3-trichloropropene | 0.0% | 3.7% | 3.8% | 1.9% | 0.2% |
| 1,1,2,2-tetrachloropropane | 0 | 0.5% | 3.3% | 29.3% | 42.1% |
| 1,2,2,3-tetrachloropropane | 0 | 13.2% | 25.4% | 46.8% | 39.2% |
| 1,1,2,3-tetrachloropropane | 0 | 0.0% | 0.0% | 3.3% | 0.0% |
| 1,1,2,2,3-pentachloropropane | 0 | 0.0% | 0.0% | 10.4% | 13.5% |
| 1,1,2,2,3,3-hexachloropropane | 0 | 0.0% | 0.0% | 0.0% | 5.0% |

EXAMPLE 7

Chlorination of 1,2,3-trichloropropene

A pressure vessel was charged with 1,2,3-trichloropropene (5 mL), aluminum chloride (0.35 g), and methylene chloride solvent (44 mL). The reactor was closed and pressure checked to 160 psig prior to initiating a flow of 30:70 $Cl_2:N_2$ gas (100 sccm) under constant stirring (800 rpm) and reactor pressure (125 psig). The reaction mixture was heated to 70° C. and then monitored by removing 1 mL aliquots at 90 and 180 minutes after the chloropropene addition. These aliquots were quenched with water and then analyzed by gas chromatography to determine the product composition, shown in Table 7, below.

TABLE 7

| | \multicolumn{3}{c}{Time (min)} | | |
|---|---|---|---|
| | 0 | 90 | final |
| | | Mol % | |
| 1,2,3-trichloropropene | 52.2% | 0.0% | 0.0% |
| 1,2,2,3-tetrachloropropane | 5.6% | 0.5% | 0.0% |
| 1,1,2,2,3-pentachloropropene | 42.2% | 69.3% | 68.3% |
| 1,1,2,2,3,3-hexachloropropane | 0.0% | 30.2% | 31.7% |

EXAMPLE 8

Chlorination of 1,2,3-trichloropropene

A pressure vessel was charged with aluminum chloride (0.15 g), iodine (0.08 g), and methylene chloride solvent (50 mL). The reactor was closed and pressure checked to 160 psig prior to initiating a flow of 30:70 $Cl_2:N_2$ gas (100 sccm) under constant stirring (800 rpm) and reactor pressure (135 psig). The reaction mixture was heated to 70° C. and then charged with 1,2,3-trichloropropene (10 mL). The reaction was monitored by removing 1 mL aliquots at 15, 30, and 90 minutes after the chloropropene addition. These aliquots were quenched with water and then analyzed by gas chromatography to determine the product composition, shown in Table 8, below.

Taken together, examples 5-8 show that the di- and trichloropropene products can be independently reintroduced to reaction conditions similar to those found in the initial ionic chlorination reactor and chlorinated to desired tri-, tetra- and pentachlorinated propanes using both ionic chlorination catalysts and free radical initiators.

TABLE 8

| | \multicolumn{4}{c}{Time (s)} | | | |
|---|---|---|---|---|
| | 0 | 901 | 1766 | 5372 |
| | | Mol % | | |
| 1,2,3-trichloropropene | 100.0% | 86.4% | 64.0% | 0.0% |
| 1,2,2,3-tetrachloropropane | 0.0% | 1.6% | 2.9% | 2.9% |
| 1,1,2,3-tetrachloropropane | 0 | 1.9% | 4.7% | 0.0% |
| 1,1,2,2,3-pentachloropropane | 0 | 10.1% | 28.4% | 82.2% |
| 1,1,2,2,3,3-hexachloropropane | 0 | 0.0% | 0.0% | 14.9% |
| unidentified heavies | | 6.0% | 12.4% | 0.0% |

The invention claimed is:
1. A process for the production of chlorinated propanes and/or propenes from a feedstream comprising 1,2-dichloropropane and comprising an ionic chlorination step, wherein the ionic chlorination step produces a product stream comprising 1,2,3-trichloropropane that is subjected to a separation step to provide a second product stream comprising at least a portion of the 1,2,3-trichloropropane and either removing the second product stream from the process or subjecting the second product stream to a first chemical base dehydrochlorination step.

2. The process of claim 1, wherein the ionic chlorination step is conducted in the presence of a catalyst comprising aluminum chloride, ferric chloride, iodine, sulfur, iron, antimony pentachloride, boron trichloride, one or more lanthanum halides, and one or more metal triflates or a combination of these.

3. The process of claim 1, wherein the ionic chlorination product stream further comprises 1,2,2,3-tetrachloropropane.

4. The process of claim 1, wherein the ionic chlorination product stream comprises trichloropropanes, tetrachloropropanes, and pentachloropropanes.

5. The process of claim 4, wherein the ionic chlorination product stream and second product stream further comprise 1,2,2,3-tetrachloropropane.

6. The process of claim 1, wherein the first chemical base dehydrochlorination step produces a mixture comprising di- and trichloropropenes.

7. The process of claim 6, wherein the chloropropenes are subjected to a further chlorination step to provide a mixture comprising tetra- and pentachloropropanes.

8. The process of claim 7, wherein the further chlorination step is conducted in the same reactor as the ionic chlorination step.

9. The process of claim 7, wherein the further chlorination step is conducted in a separate reactor without a catalyst or with a free radical initiator comprising one or more azo compounds and/or peroxide compounds, UV light, or combinations of these.

10. The process of claim 4, wherein the pentachloropropanes are separated, purified and subjected to a second dehydrochlorination step.

11. The process of claim 10, wherein the second dehydrochlorination step is conducted using one or more basic chemicals comprising caustic soda, pottasium hydroxide, calcium hydroxide or a combination of these.

12. The process of claim 11, wherein the process comprises a further dehydrochlorination step, conducted catalytically.

13. The process of claim 12, wherein the catalyst comprises a Lewis acid catalyst.

14. The process of claim 12, wherein the catalyst comprises aluminum chloride, ferric chloride, iodine, sulphur, iron, antimony pentachloride, boron trichloride, one or more lanthanum halids, and one or more metal triflates or a combination of these.

15. The process of claim 1, further comprising the use of $C_{12}$, $SO_2C_{12}$ or combinations of these as a chlorinating agent.

16. The process of claim 1, wherein one or more components of the feedstream is generated for use in the process.

17. A process for preparing 2,3,3,3-tetrafluoroprop-1-ene or 1,3,3,3-tetrafluoroprop-1-ene comprising converting a chlorinated propene prepared by the process of claim 1 into 2,3,3,3-tetrafluoroprop-1-ene or 1,3,3,3-tetrafluoroprop-1-ene.

* * * * *

UNITED STATES PATENT AND TRADEMARK OFFICE
CERTIFICATE OF CORRECTION

| | | |
|---|---|---|
| PATENT NO. | : 9,512,053 B2 | Page 1 of 1 |
| APPLICATION NO. | : 14/653503 | |
| DATED | : December 6, 2016 | |
| INVENTOR(S) | : Max M. Tirtowidjojo et al. | |

It is certified that error appears in the above-identified patent and that said Letters Patent is hereby corrected as shown below:

In the Claims

In Claim 11 (Column 18, Line 9), replace the term "pottasium" with --potassium--

Signed and Sealed this
Eighth Day of August, 2017

Joseph Matal
*Performing the Functions and Duties of the*
*Under Secretary of Commerce for Intellectual Property and*
*Director of the United States Patent and Trademark Office*